(12) United States Patent
Chattopadhyay et al.

(10) Patent No.: US 8,207,236 B2
(45) Date of Patent: Jun. 26, 2012

(54) METHOD FOR THE PRODUCTION OF POROUS PARTICLES

(75) Inventors: Pratibhash Chattopadhyay, North Royalton, OH (US); Boris Y. Shekunov, Aurora, OH (US); Adam K. Gibson, Fairlawn, OH (US)

(73) Assignee: Ferro Corporation, Cleveland, OH (US)

( * ) Notice: Subject to any disclaimer, the term of this patent is extended or adjusted under 35 U.S.C. 154(b) by 653 days.

(21) Appl. No.: 11/748,095

(22) Filed: May 14, 2007

(65) Prior Publication Data

US 2007/0275076 A1 Nov. 29, 2007

Related U.S. Application Data

(60) Provisional application No. 60/747,993, filed on May 23, 2006.

(51) Int. Cl.
C08J 9/28 (2006.01)
C08J 9/26 (2006.01)
A61K 9/14 (2006.01)

(52) U.S. Cl. ............. 521/64; 521/61; 521/56; 521/65; 521/69; 424/489

(58) Field of Classification Search .......... 424/489, 424/490; 521/61, 64, 56, 65, 69
See application file for complete search history.

(56) References Cited

U.S. PATENT DOCUMENTS

| 5,714,154 | A * | 2/1998 | Le Hen-Ferrenbach et al. | 424/401 |
|---|---|---|---|---|
| 6,270,700 | B1 * | 8/2001 | Ignatious | 264/4.1 |
| 2003/0099674 | A1 * | 5/2003 | Chen | 424/400 |
| 2004/0018240 | A1 * | 1/2004 | Ohmachi et al. | 424/486 |
| 2004/0071781 | A1 * | 4/2004 | Chattopadhyay et al. | 424/489 |
| 2007/0248541 | A1 * | 10/2007 | Tagawa et al. | 424/9.1 |

OTHER PUBLICATIONS

Jennifer Fiegel, et al. "Large Porous Particle Impingement on Lung Epithelial Cell Monolayers—Toward Improved Particle Characterization in the Lung," Pharmaceutical Research, vol. 20, No. 5, May 2003, pp. 788-796.

David A. Edwards, et al. "Large Porous Particles for Pulmonary Drug Delivery," Science, vol. 276, Jun. 20, 1997, pp. 1868-1871.

True L. Rogers, et al. "A novel particle engineering technology: spray-freezing into liquid," International Journal of Pharmaceutics 242 (2002) pp. 93-100.

Adrian I. Bot, et al. "Novel Lipid-Based Hollow-Porous Microparticles as a Platform for Immunoglobulin Delivery to the Respiratory Tract," Pharmaceutical Research, vol. 17, No. 3, 2000, pp. 275-283.

Sarma P. Duddu, et al. "Improved Lung Delivery from a Passive Dry Powder Inhaler Using an Engineered PulmoSphere® Powder," Pharmaceutical Research, vol. 19, No. 5, May 2002, pp. 689-695.

Melisa K. Barron, et al. "Investigation of Processing Parameters of Spray Freezing Into Liquid to Prepare Polyethylene Glycol Polymeric Particles for Drug Delivery," AAPS PharmSciTech 2003; 4 (2) Article 12 (http://www.pharmscitech.org), pp. 1-13.

Rita Vanbever, et al. "Sustained Release of Insulin From Insoluble Inhaled Particles," Drug Development Research 48 1999, pp. 178-185.

* cited by examiner

Primary Examiner — Vasu Jagannathan
Assistant Examiner — Irina Krylova
(74) Attorney, Agent, or Firm — Rankin, Hill & Clark LLP

(57) ABSTRACT

The present invention provides a method for the production of porous particles that involves extracting an organic solvent from a water-in-oil-in-water emulsion. In accordance with the method of the invention, a first aqueous solution including a porosity-promoting agent is emulsified into an organic solution including a therapeutic constituent and, optionally, a matrix material to form a water-in-oil emulsion. The water-in-oil emulsion is then emulsified into a second aqueous solution including a surfactant to form the water-in-oil-in-water emulsion. Extraction of the organic solvent from the water-in-oil-in-water emulsion, such as by supercritical fluid extraction, causes the therapeutic constituent and optional matrix material to precipitate and thus form an aqueous suspension of porous particles. The aqueous suspension can be centrifuged, filtered and lyophilized to obtain dry porous particles suitable for use in the deep lung delivery of drugs and other therapeutic agents.

19 Claims, 3 Drawing Sheets

METHOD FOR THE PRODUCTION OF POROUS PARTICLES

CROSS-REFERENCE TO RELATED APPLICATIONS

This application claims priority to U.S. App. Ser. No. 60/747,993, filed May 23, 2006.

BACKGROUND OF INVENTION

1. Field of Invention

The present invention relates to a method for the production of porous particles and, more particularly, to a method for the production of porous particles including a therapeutic constituent that can be effectively dosed to humans via inhalation.

2. Description of Related Art

Respiratory drug delivery ("RDD") therapy has been used for the treatment of various pulmonary disorders such as, for example, cystic fibrosis, bronchial infections, pneumonia and sinusitis. The delivery of drugs and other therapeutic constituents through the lungs allows for direct adsorption of macromolecules and small doses of hydrophobic drugs into the blood stream through the large alveolar surface and thin epithelial lining. The bioavailability of these molecules has been observed to be higher when delivered through the lungs as compared to other non-invasive delivery routes.

Although the administration of drugs via RDD is highly desirable, it has proven to be quite difficult to process some drugs into particles adequate for inhalation. One of the primary challenges includes modulation of the release of the drug(s) from the inhaled particles while simultaneously avoiding the rapid natural clearance of inhaled particles from the lungs. These challenges can be overcome by incorporating the drug in a matrix material in the form of low bulk density porous particles that have a geometric diameter within the range of from about 10 μm to about 20 μm and an equivalent aerodynamic diameter within the range of from about 1 μm to about 5 μm. Particles having these characteristics are not eliminated by alveolar macrophage clearance due to their large geometric size, enabling the drug to be used for sustained release applications in the lungs. In vitro studies of large, porous particles consisting of deslorelin, a peptide drug, in a poly-lactic-glycolic acid ("PLGA") matrix material indicated that the uptake of deslorelin into respiratory epithelial cells (Calu-3 and A549) and rat alveolar macrophages was decreased by 87%, 91%, and 50% respectively, compared to conventional small non-porous particles, suggesting the ability of these particles to avoid macrophage uptake and sustain lung delivery. See Koushik, K. and Kompella, U. B., Preparation of large porous deslorelin-PLGA microparticles with reduced residual solvent and cellular uptake using a supercritical $CO_2$ process, Pharm Res. 21:524-535 (2004).

The conventional methods of precipitating porous composite drug/matrix material particles include spray drying, evaporating or extracting solvents from emulsions, spray freezing into liquid nitrogen and supercritical fluid precipitation. Spray drying methods are generally not suitable for thermally labile materials due to the elevated temperatures involved in processing. Some emulsion-based techniques have had problems with residual solvent in the final product and the processing time for precipitating particles by evaporating a solvent from an emulsion is prohibitively long in most cases. The spray freezing technique is not suitable for processing compounds such as proteins that can be damaged due to temperature stresses.

BRIEF SUMMARY OF THE INVENTION

The present invention provides a method for the production of porous particles that are suitable for use in the deep lung delivery of drugs and other therapeutic agents. The particles produced according to the method of the invention can comprise a single substance or, more preferably, comprise a composite of two or more different substances such as a drug constituent and a matrix material. The method according to the invention can be used to produce particles having a controlled geometric particle size, a controlled equivalent aerodynamic size, a controlled pore size and porosity, a controlled particle size distribution and a defined drug loading. The method of the invention overcomes the limitations of conventional methods and provides particles that are suitable for deep lung delivery of drugs and other therapeutic agents.

In accordance with the method of the invention, a first aqueous solution is emulsified into an organic solution comprising a therapeutic constituent and, optionally, a matrix material to form a water-in-oil emulsion. The water-in-oil emulsion is then emulsified into a second aqueous solution comprising a surfactant to form the water-in-oil-in-water emulsion. The first aqueous solution and/or the second aqueous solution comprise a porosity-promoting agent. Extraction of the organic solvent from the water-in-oil-in-water emulsion, such as by supercritical fluid extraction, causes the therapeutic constituent and optional matrix material to precipitate and thus form an aqueous suspension of porous particles. The aqueous suspension can be centrifuged, filtered and lyophilized to obtain dry porous particles suitable for use in the deep lung delivery of drugs and other therapeutic agents.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
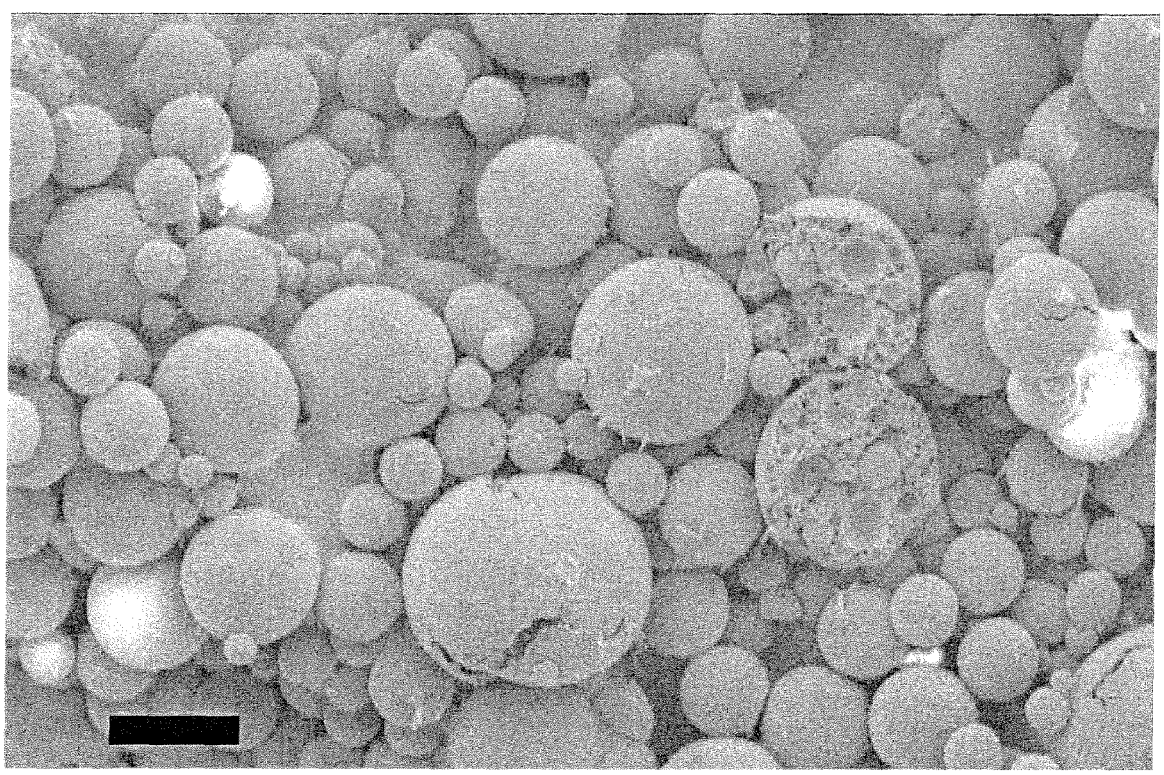
FIG. 1 is a scanning electron micrograph of particles formed in Examples 1-3.
Figure 2:
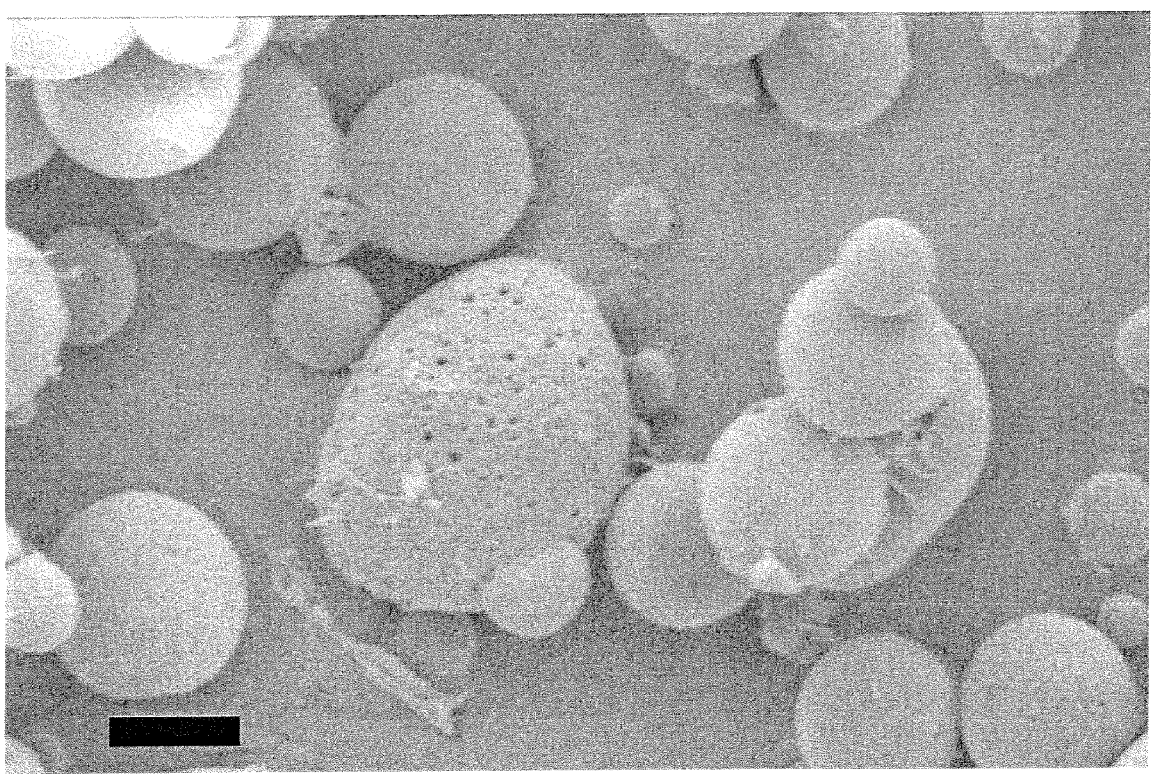
FIG. 2 is another scanning electron micrograph of particles formed in Examples 1-3.

In accordance with the method of the invention, extraction of an organic solvent from a water-in-oil-in-water ("W1/O/W2") emulsion causes a therapeutic constituent and optional matrix material to precipitate (or co-precipitate) from the "oil" phase of the W1/O/W2 emulsion and thus form an aqueous suspension of porous particles comprising the therapeutic constituent and optional matrix material. As noted, the aqueous suspension can be centrifuged, filtered and lyophilized to obtain dry porous particles of the therapeutic constituent and optional matrix material.

The first aqueous solution ("W1") and/or the second aqueous solution ("W2") comprise a porosity-promoting agent dissolved in water. Suitable porosity-promoting agents include, for example, water-soluble salts, glycerol and sugars. The presently most preferred porosity-promoting agent for use in the invention is sodium chloride, and it is preferably present only in the first aqueous solution ("W1") in an amount from about 0.1% to about 20% by weight of the first aqueous solution, and more preferably from about 1% to about 10% by weight of the first aqueous solution. The concentration of the porosity-promoting agent present in the first aqueous solution ("W1") and/or the second aqueous solution ("W2") determines the porosity of the resulting particles.

The organic solution ("O") acts as a semi permeable membrane that separates the internal aqueous phase (i.e., the phase formed from the first aqueous solution) of the W1/O/W2 emulsion from the external aqueous phase (i.e., the phase formed from the second aqueous solution) of the W1/O/W2 emulsion. The organic solution ("O") comprises a therapeutic constituent that is dissolved or suspended in one or more organic solvents. Throughout the instant specification and in the appended claims, the term "therapeutic constituent" generally refers to biologically active materials such as drugs, proteins, viral agents and other therapeutically beneficial substances.

The organic solvent or solvents present in the organic solution ("O") must be at least partially insoluble in water, and must be at least partially soluble in the extracting agent, which is preferably a supercritical fluid such as supercritical carbon dioxide. More preferably, the organic solvent or solvents present in the organic solution ("O") are insoluble in water and substantially soluble in the extracting agent. Suitable organic solvents for use in the invention include dichloromethane, ethyl acetate, chloroform, triacetin, butyl alcohol, butyl lactate, methyl propyl ketone, higher molecular weight alcohols and alkanes. The preferred organic solvents for use in the invention are dichloromethane, ethyl acetate, chloroform, with dichloromethane presently being most preferred because biodegradable polymers typically used in the preparation of controlled release therapeutic agents are readily soluble therein.

The organic solution ("O") preferably further comprises one or more optional matrix materials such as, for example, biodegradable polymers, lipids and waxes. The presence of one or more matrix materials in the organic solution ("O") leads to the formation of porous particles in which the therapeutic constituent is either coated or dispersed in the matrix material, which facilitates the timed release of the therapeutic agent into the bloodstream when the porous particles are inhaled into the lungs. Because an aqueous suspension of particles is formed, the matrix materials should be soluble or capable of being plasticized or swelled in the organic solvent(s), but should not be soluble in water. The loading of the therapeutic constituent and the optional matrix materials in the organic solution ("O") is not per se critical, and will be determined based upon the amount of matrix material and therapeutic constituent to be delivered per particle. For effective loading, the therapeutic constituent should be compatible with the matrix material. The maximum loading of the therapeutic constituent in the matrix material is thus dependant on the amount of therapeutic constituent that is thermodynamically stable with a given concentration of matrix material.

It will be appreciated that surfactants can be dispersed in the first aqueous solution ("W1"), the organic solution ("O") and/or the second aqueous solution ("W2") in order to stabilize the W1/O/W2 emulsion. Suitable surfactants for use in the first aqueous solution ("W1") and/or second aqueous solution ("W2") include, for example, poly vinyl alcohol (PVA), poly ethylene glycol (PEG), poly propylene (PPE), poly sorbates, bile salts, pluronics, tyloxipol, and alpha-tocopherol polyethylene glycol succinate (TPGS), with PVA, PPE and poly sorbate-80 presently being preferred. Suitable surfactants for use in the organic solution ("O") include, for example, lecithins and sorbitan oleates, with lecithin presently being preferred.

To form the water-in-oil-in-water emulsion, the first aqueous solution ("W1") is emulsified into the organic solution ("O") to form a water-in-oil ("W1/O") emulsion. The amount of the first aqueous solution emulsified into the organic solution is not per se critical. A preferred weight ratio of W1 to O is from about 5:95 to about 50:50, with about 20:80 being most preferred. The W1/O emulsion is then emulsified into the second aqueous solution ("W2") to form the water-in-oil-in-water ("W1/O/W2") emulsion. Again, the amount of the W1/O emulsion emulsified into the second aqueous solution is not per se critical. A preferred weight ratio of W1/O to W2 is from about 5:95 to about 50:50, with about 30:70 being most preferred. In both instances, emulsification can be accomplished using conventional emulsion techniques such as high-pressure homogenization, sonication, colloidal milling or by using a high shear mixer like an ULTRA TURRAX dispensing tool.

Porous particles that comprise at least the therapeutic constituent and optionally one or more matrix materials are formed when the organic solvent from the water-in-oil-in-water ("W1/O/W2") emulsion is extracted. Extraction of the organic solvent can be accomplished using conventional extraction techniques. More preferably, however, extraction of the organic solvent is accomplished using the supercritical fluid processing technique described in Chattopadhyay et al., U.S. Pat. No. 6,998,051. In such process, supercritical fluid extracts the supercritical fluid-soluble organic solvent from the emulsion. This leads to supersaturation and precipitation of the therapeutic constituent and optional matrix material in the form of fine porous particles suspended in water. Precipitation can be carried out either in the continuous or the batch mode. Porosity is created by the transport of water in or out of the emulsion droplet. The porosity-promoting agents in the first aqueous solution ("W1") and/or second aqueous solution ("W2"), when in excess, promote osmosis whereby water molecules are transported into or out of the droplets during precipitation. This transport of water molecules during the precipitation process leads to the formation of pores. The porosity of the particles and the size of the pores can be controlled by changing the concentration of the porosity-promoting agent inside the external and internal aqueous phases. The porosity-promoting agents control the osmotic pressure between the two aqueous phases in the water-in-oil-in-water emulsion. It is the osmosis of water from one of the aqueous phases into the other that causes porosity to be incorporated inside the particles during precipitation.

Porous particles having a mean geometric diameter within the range of from about 0.25 µm to about 50 µm can be obtained. Particles having different mean volumetric diameters can be obtained by varying the droplet (micelle) size of the emulsion, which in turn is dependant on the emulsion composition and constituent concentration. More preferably, porous particles according to the invention have a geometric diameter within the range of from about 5 µm to about 30 µm, and even more preferably from about 10 to about 20 µm, and an equivalent aerodynamic diameter within the range of from about 0.5 µm to about 5 µm, and even more preferably from about 1 µm to about 3 µm. The term "equivalent aerodynamic diameter" is defined as the diameter of a sphere of unit density (1.0 g/cm$^3$) that exhibits the same aerodynamic behavior as the particle in question.

The aqueous suspension of porous particles can be centrifuged or filtered and lyophilized to obtain dry porous particles suitable for use in the deep lung delivery of drugs and other therapeutic agents. The dry, porous particles recovered from the aqueous suspension preferably comprise a therapeutic constituent and a biodegradable matrix material such as a biodegradable polymer, lipid and/or wax. The homogeneity distribution of the therapeutic constituent in the matrix material allows for accurate dosing of the therapeutic constituent and also for the controlled time-release of the therapeutic constituent via pulmonary administration. The improved bioavailability of drugs decreases the amount and frequency by which the therapeutic constituent must be dosed to the patient, which thus reduces the residual drug concentration in the patient. Inhaled dry porous particles according to the invention should be suitable as an alternative to oral and parenteral routes for systemic delivery of therapeutic constituents such as insulin, human growth hormone, proteins, peptides, which generally can only be effectively delivered through the gastrointestinal tract or parenterally using intravenous or intramuscular injections. Furthermore, pulmonary administration of porous particles according to the invention improves targeting of drugs to affected areas in the body, preserves the efficacy of unstable therapeutic agents and increases patient comfort and compliance.

In summary, the method of the present invention provides substantial advantages over the prior art. The method can be used to produce porous particles in a continuous manner at high product yields. The porous particles produced in accordance with the method exhibit very low residual solvent contents, well below existing minimum limits. By varying the supercritical fluid conditions and the flow rate ratio between the supercritical fluid and the emulsion, one can control the efficiency of extraction of solvent from the emulsion. The process proceeds at a fast rate, producing particles in the order of minutes compared to conventional processing methods, which may require hours or days to process the same volume of material. The process does not involve the use of high temperatures, and thus does not damage or degrade thermally labile materials during processing. The process provides excellent control over particle porosity, mean geometric particle diameter and distribution and equivalent aerodynamic diameter and distribution.

The following examples are intended only to illustrate the invention, and should not be construed as imposing limitations upon the claims.

EXAMPLE 1

Aqueous Solution W1 was prepared by dissolving 0.57 grams of sodium chloride in 1.00 gram of water at room temperature.

Organic Solution O was prepared by dissolving 1.4 grams of Eudragit E100 in 3.6 grams of dichloromethane at room temperature.

Aqueous Solution W2 was prepared by dissolving 0.1 grams of polyvinyl alcohol (PVA) in 10 grams of water.

Aqueous Solution W1 was homogenized into Organic Solution 0 to form a W1/O (i.e., "W1-in-O") emulsion using an ULTRA TURRAX mixer at setting 6.

The W1/O emulsion was then homogenized into Aqueous Solution W2 to form a W1/O/W2 (i.e., "W1-in-O-in-W2") multiple emulsion using an ULTRA TURRAX mixer at setting 4. Upon examination using a light microscope the internal emulsion appeared to be stable with very small droplets below 1 micron. The multiple emulsion was however unstable with droplet coalescence and hence was continuously homogenized at ULTRA TURRAX setting 4 during processing. The stability of the W1/O/W2 emulsion likely could have been improved by changing the concentration of the surfactant in the emulsion.

EXAMPLE 2

The W1/O/W2 emulsion formed in Example 1 was introduced into an extraction chamber having a volume of 300 ml and containing supercritical $CO_2$ at 80 bar and 35° C. The extraction chamber was equipped with a mixer in order to improve extraction efficiency of the organic solvent by the supercritical fluid. Supercritical $CO_2$ was continuously introduced into the chamber in order to facilitate extraction of the organic solvent from the emulsion. The extraction chamber was maintained at a constant pressure and temperature of 80 bar and 35° C., respectively, throughout the extraction process. The flow rate of the $CO_2$ through the extraction chamber was maintained at a constant rate of 50 ml/min. The W1/O/W2 emulsion flow rate was maintained at 2 ml/min. The product (an aqueous suspension of particles) was collected in a continuous fashion using a valve attached at the bottom of the extraction chamber.

EXAMPLE 3

The aqueous suspension of particles formed in Example 2 was subjected to high speed centrifugation at 3000 rpm in order to separate the particles. The particles obtained from the centrifugation process were lyophilized in order to obtain dry particles.

Analysis of the surface morphology of the particles was performed using Scanning Electron Microscopy. FIGS. 1 and 2 are scanning electron micrographs of the particles. The particles are clearly porous. It was determined using laser light scattering technique that the polymer particles had a mean geometric diameter of 14 microns. The composite porous particles are believed to be suitable for RDD therapy.

EXAMPLE 4

Aqueous Solution W1 was prepared by dissolving 0.32 grams of sodium chloride in 1.00 g of water at room temperature.

Organic Solution O was prepared by dissolving 0.8 grams of Eudragit RS100 in 4.2 grams of dichloromethane at room temperature.

Aqueous Solution W2 was prepared by dissolving 0.9 grams of poly vinyl alcohol (PVA) and 0.9 grams of sodium chloride in 17.1 grams of water.

Aqueous Solution W1 was homogenized into Organic Solution O to form a W1/O (i.e., "W1-in-O") emulsion using an ULTRA TURRAX mixer at setting 6.

The W1/O emulsion was then homogenized into Aqueous Solution W2 to form a W1/O/W2 (i.e., "W1-in-O-in-W2") multiple emulsion using an ULTRA TURRAX mixer at setting 4. Upon examination using a light microscope the internal emulsion appeared to be stable with very small droplets below 1 micron. The multiple emulsion was also stable.

EXAMPLE 5

The dichloromethane was evaporated from the O phase of the emulsion described in Example 4, thereby forming porous particles. Evaporation was conducted at room temperature for six hours while the emulsion was stirred using a magnetic stirrer. Formation of the particles could also be easily accomplished by employing supercritical $CO_2$ to extract the dichloromethane and form the porous particles (as in Example 2).

The particles were harvested from the aqueous suspension in a manner similar to that employed in Example 3.

Figure 3:
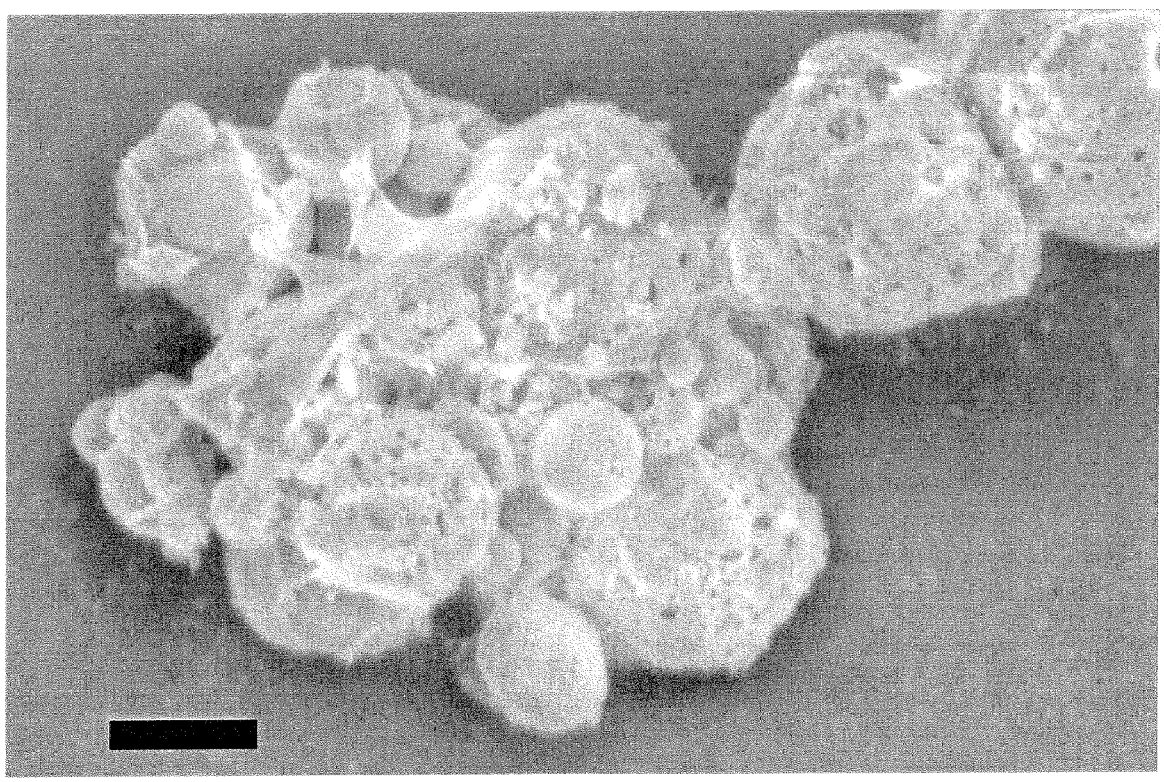
FIG. 3 is a scanning electron micrograph of particles formed in Examples 4 and 5.

Analysis of the surface morphology of the particles was performed using Scanning Electron Microscopy. FIG. 3 is a scanning electron micrograph of the particles.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of producing porous particles comprising:
providing a first aqueous solution comprising a porosity-promoting agent dissolved in water;
providing an organic solution comprising a therapeutic constituent dissolved or suspended in an organic solvent;
providing a second aqueous solution comprising a surfactant;
emulsifying the first aqueous solution into the organic solution to form a water-in-oil emulsion;
emulsifying the water-in-oil emulsion into the second aqueous solution to form a water-in-oil-in-water emulsion in which an internal aqueous phase of the water-in-oil-in-water emulsion is formed from the first aqueous solution, an oil phase of the water-in-oil-in-water emulsion is formed from the organic solution, and an external aqueous phase of the water-in-oil-in-water emulsion is formed from the second aqueous solution; and
extracting the organic solvent from the oil phase of the water-in-oil-in-water emulsion using a supercritical fluid to cause precipitation of the therapeutic constituent, said porosity-promoting agent in the internal aqueous phase promoting osmosis of water from one of the internal aqueous phase and the external aqueous phase to the other of the internal aqueous phase and the external aqueous phase during extraction and precipitation of the therapeutic constituent such that an aqueous suspension of porous particles comprising the therapeutic constituent is formed.

2. The method according to claim 1 further comprising recovering and drying the porous particles from the aqueous suspension.

3. The method according to claim 2 wherein the porous particles are recovered and dried from the aqueous suspension via centrifuging, filtering and lyophilizing.

4. The method according to claim 1 wherein the organic solution further comprises a matrix material.

5. The method according to claim 1 wherein the porosity-promoting agent is selected from the group consisting of water-soluble salts, glycerol and sugars.

6. The method according to claim 1 wherein the organic solution further comprises a co-solvent.

7. The method according to claim 1 wherein the surfactant in the second aqueous solution is selected from the group consisting of poly vinyl alcohol (PVA), poly ethylene glycol (PEG), poly propylene (PPE), poly sorbates, bile salts, pluronics, tyloxipol, and alpha-tocopherol polyethylene glycol succinate (TPGS).

8. The method according to claim 1 wherein the porous particles have a mean geometric diameter of from about 10 μm to about 20 μm and an equivalent aerodynamic diameter of from about 1 μm to about 3 μm.

9. The method according to claim 1 wherein the supercritical fluid is supercritical carbon dioxide.

10. A method of producing porous particles comprising:
providing a first aqueous solution comprising a porosity-promoting agent selected from the group consisting of water-soluble salts, glycerol and sugars dissolved in water;
providing an organic solution comprising a therapeutic constituent dissolved in a water insoluble organic solvent that is soluble in supercritical fluid extracting agent;
providing a second aqueous solution comprising a surfactant in water;
emulsifying the first aqueous solution into the organic solution to form a water-in-oil emulsion;
emulsifying the water-in-oil emulsion into the second aqueous solution to form a water-in-oil-in-water emulsion in which an internal aqueous phase of the water-in-oil-in-water emulsion is formed from the first aqueous solution, an oil phase of the water-in-oil-in-water emulsion is formed from the organic solution, and an external aqueous phase of the water-in-oil-in-water emulsion is formed from the second aqueous solution; and
extracting the organic solvent from the oil phase of the water-in-oil-in-water emulsion using the supercritical fluid extracting agent to cause precipitation of the therapeutic constituent, said porosity-promoting agent in the internal aqueous phase promoting osmosis of water from one of the internal aqueous phase and the external aqueous phase to the other of the internal aqueous phase and the external aqueous phase during extraction and precipitation of the therapeutic constituent such that an aqueous suspension of porous particles comprising the therapeutic constituent is formed.

11. The method according to claim 10 further comprising recovering and drying the porous particles from the aqueous suspension.

12. The method according to claim 11 wherein the porous particles are recovered and dried from the aqueous suspension via centrifuging, filtering and lyophilizing.

13. The method according to claim 10 wherein the porosity-promoting agent is sodium chloride.

14. The method according to claim 10 wherein the organic solvent is dichloromethane.

15. The method according to claim 10 wherein the supercritical fluid extracting agent is supercritical carbon dioxide.

16. The method according to claim 10 wherein the organic solution further comprises a matrix material.

17. The method according to claim 10 wherein the organic solution further comprises a co-solvent.

18. The method according to claim 10 wherein the porous particles have a mean geometric diameter of from about 10 μm to about 20 μm and an equivalent aerodynamic diameter of from about 1 μm to about 3 μm.

19. A method of producing porous particles comprising:
providing a first aqueous solution comprising sodium chloride dissolved in water;
providing an organic solution comprising a therapeutic constituent dissolved in dichloromethane;
providing a second aqueous solution comprising a polyvinyl alcohol dissolved in water;
emulsifying the first aqueous solution into the organic solution to form a water-in-oil emulsion;
emulsifying the water-in-oil emulsion into the second aqueous solution to form a water-in-oil-in-water emulsion in which an internal aqueous phase of the water-in-oil-in-water emulsion is formed from the first aqueous solution, an oil phase of the water-in-oil-in-water emulsion is formed from the organic solution, and an external aqueous phase of the water-in-oil-in-water emulsion is formed from the second aqueous solution; and extracting the organic solvent from the oil phase of the water-in-oil-in-water emulsion using supercritical carbon dioxide to cause precipitation of the therapeutic constituent, said sodium chloride in the internal aqueous phase promoting osmosis of water from one of the internal aqueous phase and the external aqueous phase to the other of the internal aqueous phase and the external aqueous phase during extraction and precipitation of the therapeutic constituent such that an aqueous suspension of porous particles comprising the therapeutic constituent is formed.

* * * * *